US010259827B2

(12) United States Patent
Ding et al.

(10) Patent No.: US 10,259,827 B2
(45) Date of Patent: Apr. 16, 2019

(54) BMP POTENTIATORS

(71) Applicant: NOVARTIS AG, Basel (CH)

(72) Inventors: Jian Ding, Bedford, MA (US);
Marie-Helene Larraufie, Boston, MA (US); Deborah Rothman, Westfield, NJ (US); Nik Savage, Somerville, MA (US); Shaowen Wang, Jamaica Plain, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/807,462

(22) Filed: Nov. 8, 2017

(65) Prior Publication Data
US 2018/0127436 A1 May 10, 2018

Related U.S. Application Data

(60) Provisional application No. 62/420,535, filed on Nov. 10, 2016.

(51) Int. Cl.
| C07D 498/08 | (2006.01) |
| C07D 498/18 | (2006.01) |
| A61K 31/436 | (2006.01) |
| A61K 45/06 | (2006.01) |
| A61K 31/453 | (2006.01) |

(52) U.S. Cl.
CPC .......... *C07D 498/18* (2013.01); *A61K 31/436* (2013.01); *A61K 31/453* (2013.01); *A61K 45/06* (2013.01); *C07D 498/08* (2013.01)

(58) Field of Classification Search
CPC .............................. C07D 498/08; C07D 498/18
See application file for complete search history.

(56) References Cited

U.S. PATENT DOCUMENTS

| 5,284,877 A | 2/1994 | Organ et al. |
| 6,569,867 B2 | 5/2003 | Chu et al. |

FOREIGN PATENT DOCUMENTS

| EP | 378318 A1 | 7/1990 |
| EP | 0 520 554 A2 | 12/1992 |
| WO | 1989/05304 A1 | 6/1989 |
| WO | 1991/04025 A1 | 4/1991 |
| WO | 1993/14771 A1 | 8/1993 |
| WO | 94/04148 A1 | 3/1994 |
| WO | 94/04149 A1 | 3/1994 |
| WO | 2000/058318 A1 | 10/2000 |
| WO | 2001/87884 A2 | 11/2001 |
| WO | 2012/047762 A2 | 4/2012 |
| WO | 2015/106283 A1 | 7/2015 |

OTHER PUBLICATIONS

Notification of Transmittal of the International Search Report and the Written Opinion of the International Searching Authority, or the Declaration, dated Feb. 13, 2018, issued from corresponding International Patent Application No. PCT/IB2017/056991.
Dumont, Francis et al.: "The Immunosuppresive and Toxic Effects of FK-506 are Mechanistically Related Pharmacology of a Novel Antagonist of FK-506 and Rapamycin", J. Exp. Med., Sep. 1992, vol. 176, pp. 751-760.
Fung, John J. et al.: "FK506 in Solid Organ Transplantation", The Drug Monit., Dec. 1995, vol. 17, No. 6, pp. 592-595.
Kawai, Megumi et al.: "Structure-activity profiles of macrolactum immunosuppressant FK-506 analogues", Federation of European Biochemical Societies, Jan. 1993, vol. 316, No. 2, pp. 107-113.
Long, Lu et al.: "Selective enhancement of endothelial BMPR-II with BMP9 reverses pulmonary arterial hypertension", Nature Medicine, Jul. 2015, vol. 21, No. 7, pp. 777-789.
Marinec, Paul S.:"Synthesis of orthogonally reactive FK506 derivatives via olefin cross metathesis", Bioorganic & Medicinal Chemistry, (2009), vol. 17, pp. 5763-5768.
Nambu, Mitchell et al.: "A calcineurin antifungal strategy with analogs of FK506", Bioorganic & Medicinal Chemistry Letters, (2017), vol. 27, pp. 2465-2471.
Nambu, Mitchell et al.: "A calcineurin antifungal strategy with analogs of FK506", Bioorganic & Medicinal Chemistry Letters, (2017), Accepted Manuscript, pp. 1-16.

(Continued)

*Primary Examiner* — Brian E McDowell
(74) *Attorney, Agent, or Firm* — Asimina T. Georges Evangelinos

(57) ABSTRACT

The disclosure provides compounds of Formula (I) or a pharmaceutically acceptable salt thereof, wherein:

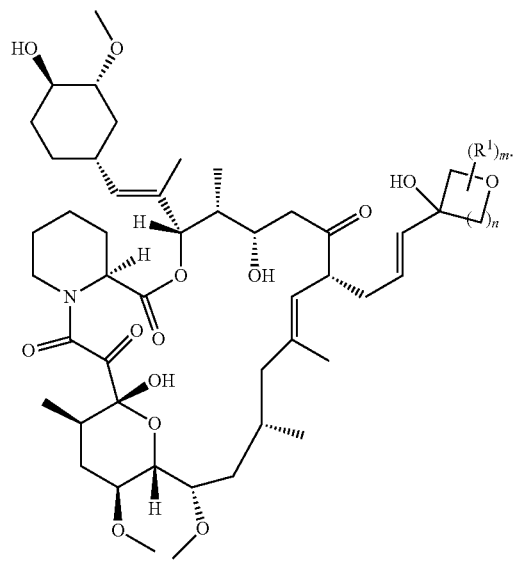

(I)

Also provided are methods of making the compounds of Formula (I) and their methods of use.

14 Claims, No Drawings

(56) References Cited

OTHER PUBLICATIONS

Spiekerkoetter, Edda et al.: "FK506 activates BMPR2, rescues endothelial dysfunction, and reverses pulmonary hypertension", The Journal of Clinical Investigation, Aug. 2013, vol. 123, No. 8, pp. 3600-3613.
Steinbicker, et al.: "Pertubation of hepcidin expression by BMP type I receptor deletion induces iron overload in mice", Blood, Oct. 13, 2011, vol. 118, No. 15, pp. 4224-4231.
Tillet, Emmanuelle et al.: "Emerging roles of BMP9 amd BMP10 in hereditary hemorrhagic telangiectasia", Frontiers in Genetics (www.frontiersin.org), Jan. 2015, vol. 5, Article 456, pp. 1-7.
Vukicevic, Slobodan et al.:"Bone Morphogenetic Protein: Systems Biology Regulators", Springer, (2017), pp. 1-448.
Wang, Richard N. et al.: "Bone Morphogenetic Protein (BMP) signaling in development and human diseases", Genes & Diseases, (2014), vol. 1, pp. 87-105.
CAS Registry No. 374595-54-7, Chemical or Trade Name: 15,19-Epoxy-3H-pyrido[2,1-c][1,4] oxaazacyclotricosine-1,7,20,21(4H,23H)-tetrone,5,6,8,11,12,13,14,15,16,17,18,19,24,25,26,26a-hexadecahydro-5,19-dihydroxy-3-[(1E)-2-[(1R,3R,4R)-4-hydroxy-3-methoxycyclohexyl]-1-methylethenyl]-16-methoxy-4,10,12,18-tetramethyl-8-(2-propenyl)-,(3S,4R,5S,8R,9E,12R,15R,16S,18R,19R,26aS)-(9CI) (CA Index Name), Entry Date: Dec. 10, 2001.
CAS Registry No. 1801372-62-2,Chemical or Trade Name: 15,19-Epoxy-3H-pyrido[2,1-c][1,4] oxaazacyclotricosine-1,7,20,21(4H,23H)-tetrone,5,6,8,11,12,13,14,15,16,17,18,19,24,25,26,26a-hexadecahydro-5,11,19-trihydroxy-3-[(1E)-2-[(1R,3R,4R)-4-hydroxy-3-methoxycyclohexyl]-1-methylethenyl]-14,16-dimethoxy-4,10,12,18-tetramethyl-8-(2-propen-1-yl)-,(3S,4R,5S,8R,9E,11S,12R,14S,15R,16S,18R,19R,26aS)—(CA Index Name), Entry Date: Aug. 4, 2015.
CAS Registry No. 137635-81-5, Chemical or Trade Name: 15,19-Epoxy-3H-pyrido[2,1-c][1,4] oxaazacyclotricosine-1,7,20,21(4H,23H)-tetrone, 5,6,8,11,12,13,14,15,16,17,18,19,24,25,26,26a-hexadecahydro-5,11,19-trihydroxy-3- [2-(4-hydroxy-3-methoxycyclohexyl)-1-methylethenyl]-8-(1-hydroxy-2-propenyl)-14,16-dimethoxy-4,10,12,18-tetramethyl-(9CI (CA Index Name), Entry Date: Nov. 29, 1991.
CAS Registry No. 124554-22-9, Chemical or Trade Name: 15,19-Epoxy-3H-pyrido[2,1-c][1,oxaazacyclotricosine-1,7,20,21(4H,23H)-tetrone, 5,6,8,11,12,13,14,15,16,17,18,19,24,25,26,26a-hexadecahydro 5,11,19-trihydroxy-3- [2-(4-hydroxy-3-methoxycyclohexyl)-1-methylethenyl]-14,16-dimethoxy-4,10,12,18-tetramethyl-8-(2-propen-1-yl)—(CA Index Name), Entry Date: Jan. 5, 1990.
CAS Registry No. 374595-53-6, Chemical or Trade Name: 15,19-Epoxy-3H-pyrido[2,1-c][1,4] oxaazacyclotricosine-1,7,20,21(4H,23H)-tetrone,5,6,8,11,12,13,14,15,16,17,18,19,24,25,26,26a-hexadecahydro-5,19-dihydroxy-3-[(1E)-2-[(1R,3R,4R)-4-hydroxy-3-methoxycyclohexyl]-1-methylethenyl]-14-methoxy-4,10,12,16,18-pentamethyl-8-(2-propenyl)-,(3S,4R,5S,8R,9E,12S,14S,15S,16S,18R,19R,26aS)-(9CI) (CA Index Name), Entry Date: Dec. 10, 2001.
CAS Registry No. 1025792-32-8, Chemical or Trade Name: 15,19-Epoxy(9E)-3H-pyrido[2,1-c][1,4] oxaazacyclotricosine-1,7,20,21(4H,23H)-tetrone, 8-ethyl-5,6,8,11,12,13,14,15,16,17,18,19,24,25,26,26a-hexadecahydro-5,11,19-trihydroxy-3-[(1E)-2-[(1R,3R,4R)-4-hydroxy-3-methoxycyclohexyl]-1-methylethenyl]-14-methoxy-4,10,12,18-tetramethyl-(3S,4R,5S,8R,12R,14S,15S,18R,19R,26aS)—(CA Index Name), Entry Date: Jun. 5, 2008.

BMP POTENTIATORS

CLAIM OF PRIORITY

This application claims priority from U.S. Ser. No. 62/420,535 filed Nov. 10, 2016, which is incorporated herein by reference in its entirety.

BACKGROUND OF THE INVENTION

Bone morphogenetic protein (BMP) signaling has been implicated in several processes during embryonic development and in adult tissue homeostasis. BMPs provide critical signals for determining cell fate, embryonic patterning, osteogenesis, chondrogenesis, iron homeostasis and are regulators of endothelial cell proliferation, migration and tube formation. Genetic studies in human and in mouse show that perturbations in BMP signaling lead to various diseases. Mutations in BMP type II and type I receptors have been linked to pulmonary arterial hypertension (PAH) (Long et al. *Nature Medicine* 21:777-784, 2015), and hereditary hemorrhagic telangiectasia (HHT) (Tillet et al. *Front. Genet.* 8(5): 456, 2015; Wang et al. *Genes & Diseases* 1:87-105, 2014), also known as Osler-Weber-Rendu disease and Osler-Weber-Rendu syndrome, respectively. Deficiency of BMP signaling is also involved in kidney injury, proteinuric diseases, and iron overload anemia (Sampath et al. (2017) Bone Morphogenetic Protein-7 and Its Role in Acute Kidney Injury and Chronic Kidney Failure; Vukicevic S., Sampath K. (eds) Bone Morphogenetic Proteins: Systems Biology Regulators; Progress in Inflammation Research. Springer, Cham; Steinbicker et al. Blood 118(15): 4224-4230).

Further, HHT is an inherited autosome dominant vascular dysplasia affecting 1:5000/8000 people worldwide. Hallmark features include recurrent epistaxis (nosebleed) and/or chronic GI blood loss due to telangiectasias (small dilated blood vessels) of mucosal surfaces and arteriovenous malformations (AVM) in solid organs. Larger AVMs occur in lungs (40-60% of affected individuals), liver (40-70%), brain (10%) and spine (1%). Management of HHT has largely been procedural to control the symptoms. All mutations identified in HHT patients to date affect the BMP pathway, including Endoglin (ENG) (HHT1, ~45%), Acvrl1 (ALK1) (HHT2, ~42%), and SMAD4 (Juvenile Polyposis & HHT, ~1-2%). These mutations result in haploinsufficiency of functional proteins, which cause the pathophysiology of HHT manifested as fragile vessels, capillary overgrowth and numerous AVMs. Potentiating BMP signaling would normalize the pathway signaling in vascular cells of HHT patients, to prevent the formation of new lesions and support involution of existing telangiectasias.

BMP-7 is expressed in all parts of the normal kidney parenchyma, being highest in the epithelium of proximal tubules. It protects kidney against acute and chronic injury, inflammation and fibrosis. Diabetic nephropathy is the leading cause of chronic kidney disease. Clinical data from 30 patients with diabetic nephropathy (showing increased expression of BMP-7 at initial stages of diabetic nephropathy with subsequent decrease at advanced stage) highlights the role of BMP-7 in the protection of kidney structure and function (Ivanac-Jankovic et al. *Acta Clin Croat.* 54(2): 164-8, 2015).

FK506 is a potent BMP potentiator, as it displaces FKBP12 from BMP type I receptors, thus unblocking their phosphorylation site (Spiekerkoetter et al. *J. Clin. Invest.* 123(8):3600-3613, 2013). In addition, FK506 is an immunosuppressive 23-membered macrolide lactone natural product, and has been used clinically in solid organ transplants. FK506 inhibits calcineurin activity by a unique, small molecule-mediated, protein-protein interaction. FK506 binds to FKBP12, and this binary complex binds to calcineurin and blocks dephosphorylation of pNFAT in mammals leading to immunosuppression. (Nambu et al. *Bioorganic & Medicinal Chemistry Letters* 27: 2465-2471, 2017). However, pharmacologically, calcineurin inhibition by FK506 is not required to potentiate BMP signaling. (Dumont et al. *J. Exp. Med.* 176:751-760, 1992). The majority of clinical toxicities, including nephrotoxicity, of FK506 and FK506 analogs are associated with calcineurin inhibition. Therefore, calcineurin-sparing FK506 analogs should have an improved therapeutic index. As such, there remains a need for new treatments and therapies for renal diseases, HHT and other disorders related to BMP signaling deficiency that potentiate BMP signaling, but are calcineurin-sparing.

SUMMARY OF THE INVENTION

The disclosure provides, inter alia, compounds, pharmaceutically acceptable salts thereof, pharmaceutical compositions thereof and pharmaceutical combinations thereof, which are calcineurin-sparing BMP potentiators. The disclosure further provides methods of treating, preventing, or ameliorating a disease or disorder related to BMP signaling deficiency, the method comprising administering to a subject in need thereof a therapeutically effective amount of a calcineurin-sparing BMP potentiator. In an embodiment, the disease or disorder is a renal disorder. In an embodiment, the renal disorder is selected from the group consisting of diabetic nephropathy; AKI (acute kidney injury); and proteinuric diseases. In an embodiment, the disease or disorder is selected from the group consisting of PAH (pulmonary arteria hypertension); HHT (hereditary hemorrhagic telangiectasia); iron overload anemia; fracture healing; macular degeneration (e.g., AMD (age-related macular degeneration)); glaucoma; colitis; IBD (inflammatory bowel disease); juvenile polyposis syndrome; and fibrosis (e.g., lung, liver and kidney).

In one aspect, provided herein are compounds of Formula (I) or a pharmaceutically acceptable salt thereof, wherein:

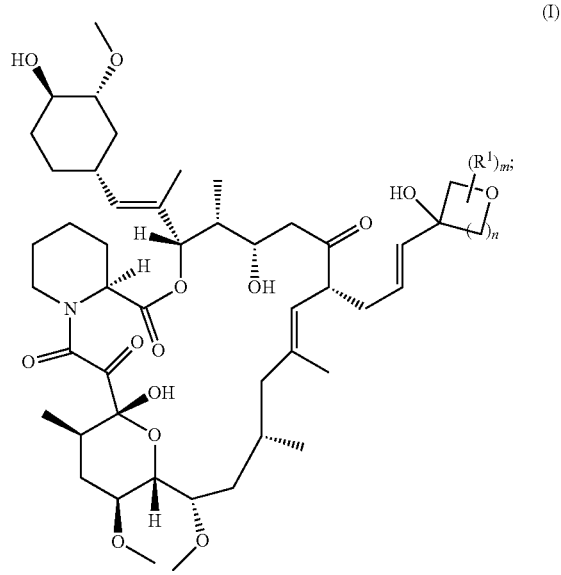

(I)

each $R^1$ is independently selected from the group consisting of halo, cyano, $C_{1-6}$alkyl, $C_{1-6}$ alkoxyl, $C_{2-6}$ alkenyl, $C_{2-6}$ alkynyl, hetero$C_{1-10}$ alkyl, and $C_{1-6}$ haloalkyl;

n is 1, 2, 3, 4, or 5; and m is 0, 1, 2, 3, or 4.

In an embodiment, n is 1, 2 or 3. In an embodiment, n is 1 or 2. In an embodiment, n is 1.

In an embodiment, $R^1$ is independently selected from the group consisting of halo and $C_{1-6}$ alkyl. In an embodiment, $R^1$ is independently $C_{1-6}$alkyl. In an embodiment, $R^1$ is independently hetero$C_{1-10}$ alkyl.

In an embodiment, m is 0 or 1. In an embodiment, m is 0. In an embodiment, n is 1 and m is 0.

In an embodiment, the compound is compound (A):

(A)

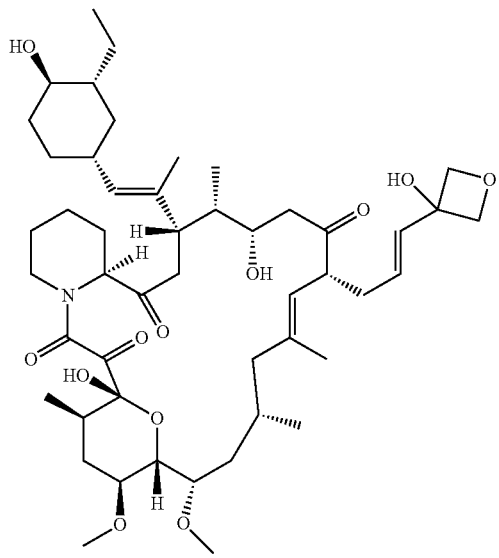

or a pharmaceutically acceptable salt thereof.

In another aspect, provided herein are compounds of Formula (II) or a pharmaceutically acceptable salt thereof, wherein:

(II)

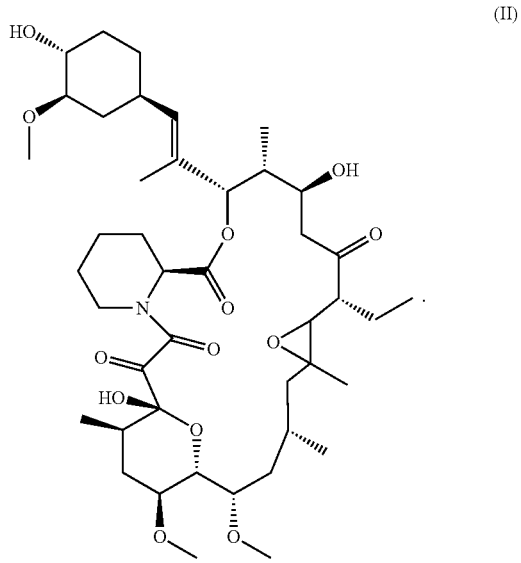 [SMILES: CC[C@H]1C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C[C@@H](C)CC3(C)OC13)[C@@H](OC)C[C@H]2C]

In an embodiment, the compound is compound (B):

(B)

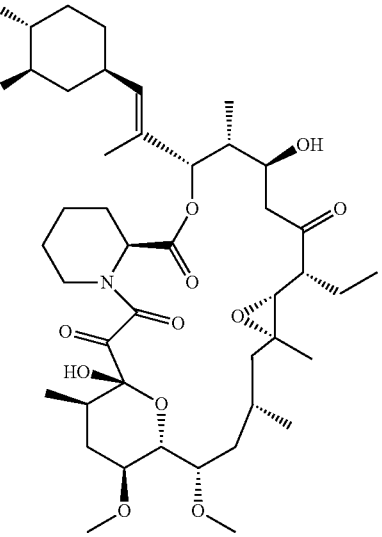

or a pharmaceutically acceptable salt thereof.

In an embodiment, the compound is compound (C):

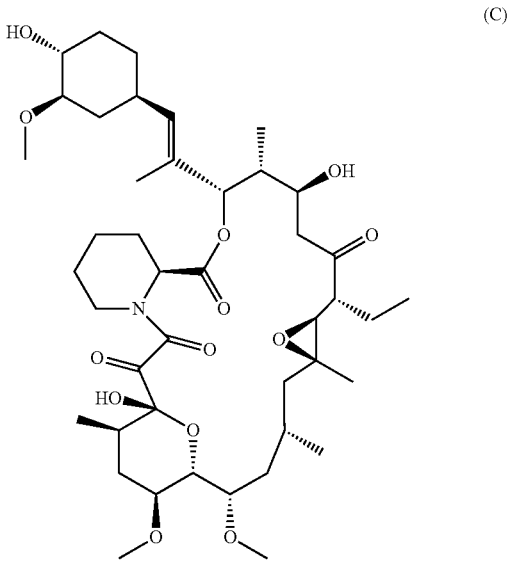 [SMILES: CC[C@H]1C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C[C@@H](C)C[C@]3(C)O[C@@H]13)[C@@H](OC)C[C@H]2C]

(C)

or a pharmaceutically acceptable salt thereof.

In another aspect, the disclosure provides a pharmaceutical composition comprising a therapeutically effective amount of a compound of Formula (I), (II), compound (A), compound (B), or compound (C) or a pharmaceutically acceptable salt thereof, and one or more pharmaceutically acceptable carriers.

In another aspect, the disclosure provides a pharmaceutical combination comprising a therapeutically effective amount of a compound of Formula (I), (II), compound (A), compound (B), or compound (C) or a pharmaceutically acceptable salt thereof, and one or more therapeutically active agents.

In another aspect, the disclosure provides a method of potentiating bone morphogenetic protein (BMP) signaling in a subject in need thereof, the method comprising administering to the subject a therapeutically effective amount of a compound of Formula (I), (II), compound (A), compound (B), or compound (C) or a pharmaceutically acceptable salt thereof; a pharmaceutical composition comprising a compound of Formula (I), (II), compound (A), compound (B), or compound (C) or a pharmaceutically acceptable salt thereof and one or more pharmaceutically acceptable carriers; or a pharmaceutical combination comprising a compound of Formula (I), (II), compound (A), compound (B), or compound (C) or a pharmaceutically acceptable salt thereof, and one or more therapeutically active agents.

In another aspect, the disclosure provides a method of treating hereditary hemorrhagic telangiectasia (HHT) in a subject in need thereof, the method comprising administering to the subject a therapeutically effective amount of a compound of Formula (I), (II), compound (A), compound (B), or compound (C) or a pharmaceutically acceptable salt thereof and one or more pharmaceutically acceptable carriers; or a pharmaceutical combination comprising a compound of Formula (I), (II), compound (A), compound (B), or compound (C) or a pharmaceutically acceptable salt thereof, and one or more therapeutically active agents.

In another aspect, the disclosure provides a method of treating renal disease in a subject in need thereof, the method comprising administering to the subject a therapeutically effective amount of a compound of Formula (I), (II), compound (A), compound (B), or compound (C) or a pharmaceutically acceptable salt thereof and one or more pharmaceutically acceptable carriers; or a pharmaceutical combination comprising a compound of Formula (I), (II), compound (A), compound (B), or compound (C) or a pharmaceutically acceptable salt thereof, and one or more therapeutically active agents.

In an embodiment, the renal disease is selected from the group consisting of diabetic nephropathy; AKI (acute kidney injury); and proteinuric diseases.

In another aspect, the disclosure provides a method of treating a disease or disorder associated with deficient BMP signaling in a subject in need thereof, the method comprising administering to the subject a therapeutically effective amount of a compound of Formula (I), (II), compound (A), compound (B), or compound (C) or a pharmaceutically acceptable salt thereof and one or more pharmaceutically acceptable carriers; or a pharmaceutical combination comprising a compound of Formula (I), (II), compound (A), compound (B), or compound (C) or a pharmaceutically acceptable salt thereof, and one or more therapeutically active agents.

In an embodiment, the disease or disorder is selected from the group consisting of PAH (pulmonary arteria hypertension); HHT (hereditary hemorrhagic telangiectasia); iron overload anemia; fracture healing; macular degeneration (e.g., AMD (age-related macular degeneration); glaucoma; dry eye; colitis; IBD (inflammatory bowel disease); juvenile polyposis syndrome; and fibrosis (e.g., lung, liver and kidney).

In another aspect, the disclosure provides a compound of Formula (I), (II), compound (A), compound (B), or compound (C) or a pharmaceutically acceptable salt thereof and one or more pharmaceutically acceptable carriers; or a pharmaceutical combination comprising a compound of Formula (I), (II), compound (A), compound (B), or compound (C) or a pharmaceutically acceptable salt thereof, and one or more therapeutically active agents, for use as a medicament.

In another aspect, the disclosure provides a compound of Formula (I), (II), compound (A), compound (B), or compound (C) or a pharmaceutically acceptable salt thereof and one or more pharmaceutically acceptable carriers; or a pharmaceutical combination comprising a compound of Formula (I), (II), compound (A), compound (B), or compound (C) or a pharmaceutically acceptable salt thereof, and one or more therapeutically active agents, for use in the treatment of hereditary hemorrhagic telangiectasia (HHT) in a subject in need thereof.

In another aspect, the disclosure provides a compound of Formula (I), (II), compound (A), compound (B), or compound (C) or a pharmaceutically acceptable salt thereof and one or more pharmaceutically acceptable carriers; or a pharmaceutical combination comprising a compound of Formula (I), (II), compound (A), compound (B), or compound (C) or a pharmaceutically acceptable salt thereof, and one or more therapeutically active agents, for use in the treatment of renal disease in a subject in need thereof.

In an embodiment, the renal disease is selected from the group consisting of diabetic nephropathy; AKI (acute kidney injury); and proteinuric diseases.

In another aspect, the disclosure provides a compound of Formula (I), (II), compound (A), compound (B), or compound (C) or a pharmaceutically acceptable salt thereof and one or more pharmaceutically acceptable carriers; or a pharmaceutical combination comprising a compound of Formula (I), (II), compound (A), compound (B), or compound (C) or a pharmaceutically acceptable salt thereof, and one or more therapeutically active agents, for use in the treatment of a disease or disorder associated with deficient BMP signaling in a subject in need thereof.

In an embodiment, the disease or disorder is selected from the group consisting of PAH (pulmonary arteria hypertension); HHT (hereditary hemorrhagic telangiectasia); iron overload anemia; fracture healing; macular degeneration (e.g., AMD (age-related macular degeneration)); glaucoma; dry eye; colitis; IBD (inflammatory bowel disease); juvenile polyposis syndrome; and fibrosis (e.g., lung, liver and kidney).

In another aspect, the disclosure provides a use of Formula (I), (II), compound (A), compound (B), or compound (C) or a pharmaceutically acceptable salt thereof and one or more pharmaceutically acceptable carriers; or a pharmaceutical combination comprising a compound of Formula (I), (II), compound (A), compound (B), or compound (C) or a pharmaceutically acceptable salt thereof, and one or more therapeutically active agents, in the manufacture of a medicament for the treatment of hereditary hemorrhagic telangiectasia (HHT) in a subject in need thereof.

In another aspect, the disclosure provides a use of Formula (I), (II), compound (A), compound (B), or compound (C) or a pharmaceutically acceptable salt thereof and one or more pharmaceutically acceptable carriers; or a pharmaceutical combination comprising a compound of Formula (I), (II), compound (A), compound (B), or compound (C) or a pharmaceutically acceptable salt thereof, and one or more therapeutically active agents, in the manufacture of a medicament for the treatment of renal disease in a subject in need thereof.

In an embodiment, the renal disease is selected from the group consisting of diabetic nephropathy; AKI (acute kidney injury); and proteinuric diseases.

In another aspect, the disclosure provides a use of Formula (I), (II), compound (A), compound (B), or compound (C) or a pharmaceutically acceptable salt thereof and one or more pharmaceutically acceptable carriers; or a pharmaceutical combination comprising a compound of Formula (I), (II), compound (A), compound (B), or compound (C) or a pharmaceutically acceptable salt thereof, and one or more therapeutically active agents, in the manufacture of a medicament for the treatment of a disease or disorder associated with deficient BMP signaling in a subject in need thereof.

In an embodiment, the disease or disorder is selected from the group consisting of PAH (pulmonary arteria hypertension); HHT (hereditary hemorrhagic telangiectasia); iron overload anemia; fracture healing; macular degeneration (e.g., AMD (age-related macular degeneration)); glaucoma; dry eye; colitis; IBD (inflammatory bowel disease); juvenile polyposis syndrome; and fibrosis (e.g., lung, liver and kidney).

The details of one or more embodiments of the invention are set forth herein. Other features, objects, and advantages of the disclosure will be apparent from the Detailed Description, the Examples, and the Claims.

DETAILED DESCRIPTION

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer.

Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$).

The term "haloalkyl" refers to a substituted alkyl group, wherein one or more of the hydrogen atoms are independently replaced by a halogen, e.g., fluoro, bromo, chloro, or iodo and includes alkyl moieties in which all hydrogens have been replaced by halo (e.g., perfluoroalkyl). In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CF_3$, —$CF_2CF_3$, —$CF_2CF_2CF_3$, —$CCl_3$, —$CFCl_2$, —$CF_2Cl$, and the like.

The terms "alkylamino" and "dialkylamino" refer to —NH(alkyl) and —NH(alkyl)$_2$ radicals, respectively. In some embodiments, the alkylamino is a —NH($C_1$-$C_4$ alkyl). In some embodiments, the alkylamino is methylamino, ethylamino, propylamino, isopropylamino, n-butylamino, iso-butylamino, sec-butylamino or tert-butylamino. In some embodiments, the dialkylamino is —NH($C_1$-$C_6$ alkyl)$_2$. In some embodiments, the dialkylamino is a dimethylamino, a methylethylamino, a diethylamino, a methylpropylamino, a methylisopropylamino, a methylbutylamino, a methylisobutylamino or a methyltertbutylamino.

The term "alkoxy" or "alkoxyl" refers to an —O-alkyl radical. In some embodiments, the alkoxy groups are methoxy, ethoxy, n-propoxy, isopropoxy, n-butoxy, tert-butoxy, sec-butoxy, n-pentoxy, n-hexoxy, and 1,2-dimethylbutoxy. In some embodiments, alkoxy groups are lower alkoxy, i.e., with between 1 and 6 carbon atoms. In some embodiments, alkoxy groups have between 1 and 4 carbon atoms.

"Hydroxyalkyl" or "hydroxylalkyl" can include alkyl structures that are substituted with one or more hydroxyl groups.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH₃ or 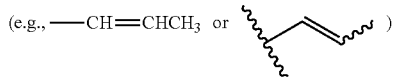 ) may be an (E)- or (Z)-double bond.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that result in the formation of a stable compound. The disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. The disclosure is not intended to be limited in any manner by the exemplary substituents described herein.

Exemplary carbon atom substituents include, but are not limited to, halogen, —CN, —NO₂, —N₃, —SO₂H, —SO₃H, —OH, —OR$^{aa}$, —ON(R$^{bb}$)₂, —N(R$^{bb}$)₂, —N(R$^{bb}$)₃⁺X⁻, —N(OR$^c$)R$^{bb}$, —SH, —SR$^{aa}$, —SSR$^{cc}$, —C(=O)R$^{aa}$, —CO₂H, —CHO, —C(OR$^{cc}$)₂, —CO₂R$^{aa}$, —OC(=O)R$^{aa}$, —OCO₂R$^{aa}$, —C(=O)N(R$^{bb}$)₂, —OC(=O)N(R$^{bb}$)₂, —NR$^{bb}$C(=O)R$^{aa}$, —NR$^{bb}$CO₂R$^{aa}$, —NR$^{bb}$C(=O)N(R$^{bb}$)₂, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)₂, —OC(=NR$^{bb}$)N(R$^{bb}$)₂, —NR$^{bb}$C(=NR$^{bb}$)N(R$^{bb}$)₂, —C(=O)NR$^{bb}$SO₂R$^{aa}$, —NR$^{bb}$SO₂R$^{aa}$, —SO₂N(R$^{bb}$)₂, —SO₂R$^{aa}$, —SO₂OR$^{aa}$, —OSO₂R$^{aa}$, —S(=O)R$^{aa}$, —OS(=O)R$^{aa}$, —Si(Ru$^{aa}$)₃, —OSi(Ru$^{aa}$)₃, —C(=S)N(R$^{bb}$)₂, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)₂, —P(=O)(OR$^{cc}$)₂, —OP(=O)(R$^{aa}$)₂, —OP(=O)(OR$^{cc}$)₂, —P(O)(N(R$^{bb}$)₂)₂, —OP(=O)(N(R$^{bb}$)₂)₂, —NR$^{bb}$(=O)(R$^{aa}$), —NR$^{bb}$P(=O) (OR$^{cc}$)₂, —NR$^{bb}$P(=O)(N(R$^{bb}$)₂)₂, —P(R$^{cc}$)₂, —P(OR$^{cc}$)₂, —P(R$^{cc}$)₃⁺X⁻, —P(OR$^{cc}$)₃⁺X⁻, —P(R$^{cc}$)₄, —P(OR$^{cc}$)₄, —OP(R$^{cc}$)₂, —OP(R$^{cc}$)₃⁺X⁻, —OP(OR$^{cc}$)₂, —OP(OR$^{cc}$)₃⁺X⁻, —OP(R$^{cc}$)₄, —OP(OR$^{cc}$)₄, —B(R$^{aa}$)₂, —B(OR$^{cc}$)₂, —BR$^{aa}$(OR$^{cc}$), $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X⁻ is a counterion;

or two geminal hydrogens on a carbon atom are replaced with the group =O, =S, =NN(R$^{bb}$)₂, =NNR$^{bb}$C(=O) R$^{aa}$, =NNR$^{bb}$C(=O)OR$^{aa}$, =NNR$^{bb}$S(=O)₂R$^{aa}$, =NR$^{bb}$, or =NOR$^{cc}$;

each instance of R$^{aa}$ is, independently, selected from $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)₂, —CN, —C(=O)R$^{aa}$, —C(=O)N(R$^{cc}$)₂, —CO₂R$^{aa}$, —SO₂R$^{aa}$, —C(=NR$^{cc}$) OR$^{aa}$, —C(=NR$^{cc}$)N(R$^{cc}$)₂, —SO₂N(R$^{cc}$)₂, —SO₂R$^{cc}$, —SO₂OR$^{cc}$, —SOR$^{aa}$, —C(=S)N(R$^{cc}$)₂, —C(=O)SR$^{cc}$, —C(=S)SR$^{cc}$, —P(=O)(R$^{aa}$), —P(=O)(OR$^{cc}$)₂, —P(=O)(N(R$^{cc}$)₂)₂, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X⁻ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$), —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal $R^{dd}$ substituents can be joined to form =O or =S; wherein X$^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^9$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$alkyl, —ON(C$_{1-6}$alkyl)$_2$, —N(C$_{1-6}$ alkyl)$_2$, —N(C$_{1-6}$ alkyl)$_3^+$X$^-$, —NH(C$_{1-6}$alkyl)$_2^+$X$^-$, —NH$_2$(C$_{1-6}$alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$alkyl), —C(=O)NH$_2$, —C(=O)N(C$_{1-6}$alkyl)$_2$, —OC(=O)NH(C$_{1-6}$ alkyl), —NHC(=O)(C$_{1-6}$alkyl), —N(C$_{1-6}$alkyl)C(=O)(C$_{1-6}$alkyl), —NHCO$_2$(C$_{1-6}$alkyl), —NHC(=O)N(C$_{1-6}$alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$alkyl)$_3$, —OSi(C$_{1-6}$alkyl)$_3$-C(=S)N(C$_{1-6}$alkyl)$_2$, C(=S)NH(C$_{1-6}$ alkyl), C(=S)NH$_2$, —C(=O)S(C$_{1-6}$alkyl), —C(=S)SC$_{1-6}$alkyl, —SC(=S)SC$_{1-6}$alkyl, —P(=O)(OC$_{1-6}$ alkyl)$_2$, —P(=O)(C$_{1-6}$ alkyl)$_2$, —OP(=O)(C$_{1-6}$alkyl)$_2$, —OP(=O)(OC$_{1-6}$ alkyl)$_2$, C$_{1-6}$alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X$^-$ are as defined herein.

Compounds

Described herein are compounds, pharmaceutical compositions and pharmaceutical combinations that potentiate BMP signaling. In an embodiment, provided is a compound of Formula (I), (II), compound (A), compound (B), or compound (C) or a pharmaceutically acceptable salt thereof.

In one aspect, provided herein are compounds of Formula (I) or pharmaceutically acceptable salt thereof, wherein:

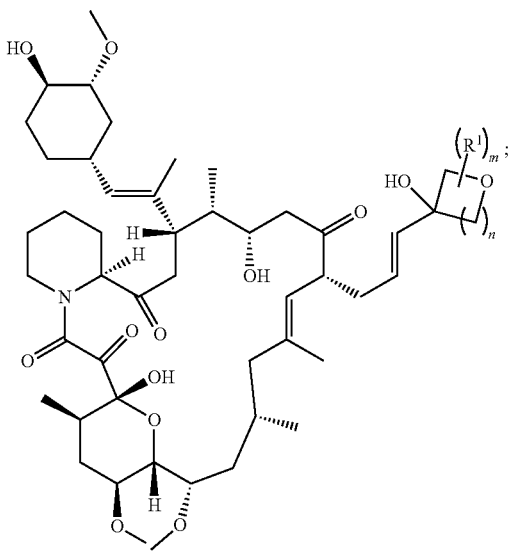

(I)

each R[1] is independently selected from the group consisting of halo, cyano, $C_{1-6}$ alkyl, $C_{1-6}$ alkoxyl, $C_{2-6}$ alkenyl, $C_{2-6}$ alkynyl, heteroC$_{1-10}$ alkyl, and $C_{1-6}$ haloalkyl;

n is 1, 2, 3, 4, or 5; and m is 0, 1, 2, 3, or 4.

In an embodiment, n is 1, 2 or 3. In an embodiment, n is 1 or 2. In an embodiment, n is 1.

In an embodiment, R[1] is independently selected from the group consisting of halo and $C_{1-6}$ alkyl. In an embodiment, R[1] is independently $C_{1-6}$alkyl. In an embodiment, R[1] is independently heteroC$_{1-10}$ alkyl.

In an embodiment, m is 0 or 1. In an embodiment, m is 0.

In a first embodiment, the invention is the compound (A) or a pharmaceutically acceptable salt thereof, wherein the compound is:

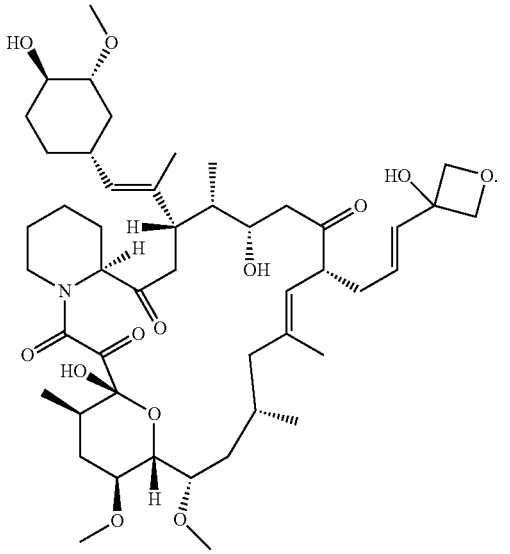

(A)

In another aspect, provided herein are compounds of Formula (II) or a pharmaceutically acceptable salt thereof, wherein:

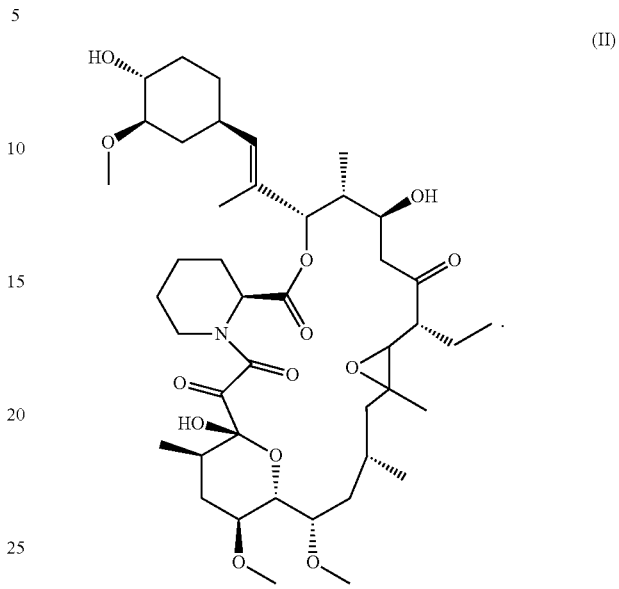

(II)

In a second embodiment, the invention is the compound (B) or a pharmaceutically acceptable salt thereof, wherein the compound is:

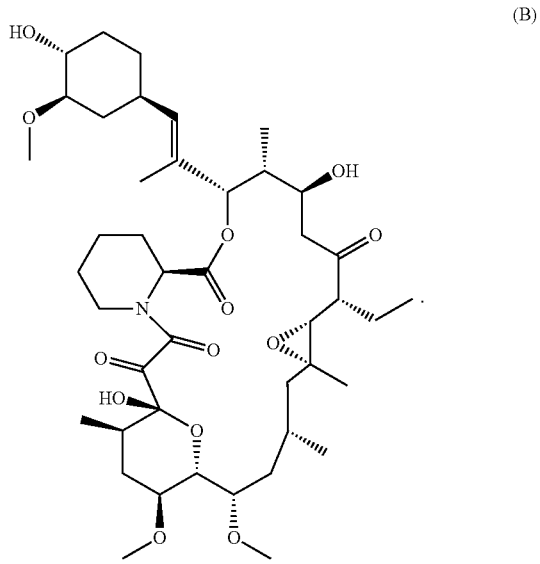 [SMILES: CC[C@H]1C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C[C@@H](C)C[C@@]3(C)O[C@H]13)[C@@H](OC)C[C@H]2C]

(B)

In a third embodiment, the invention is a pharmaceutical composition comprising a therapeutically effective amount of a compound according to any one of the first or second embodiments, or a pharmaceutically acceptable salt thereof and one or more pharmaceutically acceptable carriers.

In a fourth embodiment, the invention is a combination comprising a therapeutically effective amount of a compound according to any one of the first or second embodiments or a pharmaceutically acceptable salt thereof and one or more therapeutically active agents. In certain such embodiments, the combination is a pharmaceutical combination.

In a fifth embodiment, the invention is a method of potentiating BMP signaling in a subject in need thereof, wherein the method comprises administering to the subject a therapeutically effective amount of the compound according to any one of the first or second embodiments or a pharmaceutically acceptable salt thereof.

In a sixth embodiment, the invention is a method of treating hereditary hemorrhagic telangiectasia (HHT) and related conditions comprising administering to the subject a therapeutically effective amount of the compound according to any one of the first or second embodiments or a pharmaceutically acceptable salt thereof.

In a seventh embodiment, the invention is a compound according to any one of the first or second embodiments, or a pharmaceutically acceptable salt thereof, for use as a medicament.

In an eighth embodiment, the invention is a compound according to any one of the first or second embodiments, or a pharmaceutically acceptable salt thereof, for use in the treatment of hereditary hemorrhagic telangiectasia (HHT) and related conditions.

In a ninth embodiment, the invention is the use of a compound according to any one of the first or second embodiments, or a pharmaceutically acceptable salt thereof in the manufacture of a medicament for the treatment of hereditary hemorrhagic telangiectasia and related conditions.

In a tenth embodiment, the invention is a method of treating renal disease comprising administering to the subject a therapeutically effective amount of the compound according to any one of the first or second embodiments or a pharmaceutically acceptable salt thereof. In an embodiment, the renal disease is selected from the group consisting of diabetic nephropathy; AKI (acute kidney injury); and proteinuric diseases.

In an eleventh embodiment, the invention is a compound according to any one of the first or second embodiments, or a pharmaceutically acceptable salt thereof, for use in the treatment of renal disease. In an embodiment, the renal disease is selected from the group consisting of diabetic nephropathy; AKI (acute kidney injury); and proteinuric diseases.

In a twelfth embodiment, the invention is a use of a compound according to any one of the first or second embodiments, or a pharmaceutically acceptable salt thereof, in the manufacture of a medicament for the treatment of renal disease. In an embodiment, the renal disease is selected from the group consisting of diabetic nephropathy; AKI (acute kidney injury); and proteinuric diseases.

As used herein, the terms "salt" or "salts" refer to an acid addition or base addition salt of a compound of the invention. "Salts" include in particular "pharmaceutical acceptable salts." The term "pharmaceutically acceptable salts" refers to salts that retain the biological effectiveness and properties of the compounds disclosed herein and, which typically are not biologically or otherwise undesirable. In many cases, the compounds disclosed herein are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the disclosure provides a compound of Formula (I), (II), compound (A), compound (B), or compound (C) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In an embodiment, the disclosure provides compound (A) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In an embodiment, the disclosure provides compound (B) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the disclosure provides compound (A) and compound (B) in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

In an embodiment, the disclosure provides compound (A) in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

In an embodiment, the disclosure provides compound (B) in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

A compound of Formula (I), (II), compound (A), compound (B), or compound (C) or a pharmaceutically acceptable salt thereof is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$, $^{125}I$, respectively. The disclosure includes various isotopically labeled compounds as defined herein, for example, those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of Formula (I), (II), compound (A), compound (B), or compound (C) or a pharmaceutically acceptable salt thereof can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example, increased in vivo half-life or reduced dosage requirements or an improvement in therapeutic index. It is understood that deuterium in this context is regarded as a substituent of a compound of Formula (I), (II), compound (A), compound (B), or compound (C) or a pharmaceutically acceptable salt thereof. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the disclosure include those wherein the solvent of crystallization may be isotopically substituted, e.g. $D_2O$, $d_6$-acetone, $d_6$-DMSO.

A compound of Formula (I), (II), compound (A), compound (B), or compound (C) or a pharmaceutically acceptable salt thereof that contains groups capable of acting as donors and/or acceptors for hydrogen bonds may be capable of forming co-crystals with suitable co-crystal formers. These co-crystals may be prepared from a compound of Formula (I), (II), compound (A), compound (B), or compound (C) or a pharmaceutically acceptable salt thereof by known co-crystal forming procedures. Such procedures include grinding, heating, co-subliming, co-melting, or contacting in solution a compound of Formula (I), (II), compound (A), compound (B), or compound (C) or a pharmaceutically acceptable salt thereof with the co-crystal formed under crystallization conditions and isolating co-crystals thereby formed. Suitable co-crystal formers include those described in WO 2004/078163, which is incorporated herein by reference in its entirety. Hence, the disclosure further provides co-crystals comprising a compound of Formula (I), (II), compound (A), compound (B), or compound (C) or a pharmaceutically acceptable salt thereof.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of Formula (I), (II), compound (A), compound (B), or compound (C) or a pharmaceutically acceptable salt thereof refers to an amount of the compound that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of a compound of Formula (I), (II), compound (A), compound (B), or compound (C) or a pharmaceutically acceptable salt thereof that, when administered to a subject, is effective to (1) at least partially alleviate, inhibit, prevent and/or ameliorate a condition, or a disorder or a disease (i) mediated by BMP, or (ii) associated with BMP activity, or (iii) characterized by activity (normal or abnormal) of BMP; or (2) enhance or potentiate BMP signaling. In another non-limiting embodiment, the term "a therapeutically effective amount" refers to the amount of a compound of Formula (I), (II), compound (A), compound (B), or compound (C) or a pharmaceutically acceptable salt thereof that, when administered to a cell, or a tissue, or a non-cellular biological material, or a medium, is effective to at least partially enhance or potentiate BMP signaling.

The term "BMP potentiator" as used herein means an agent that (measurably) enhances BMP signaling, by sequestering FKBP12, to a level that is at least about 10%, at least about 15%, at least about 20%, about 25%, about 30%, about 35% about 40%, about 45%, about 50%, about 55%, about 60%, about 65%, about 70%, about 75%, about 80%, about 85%, about 90%, about 95%, about 100%, about 120%, about 150%, about 200%, about 250%, about 300%, about 350%, about 400%, about 450%, or about 500% more than the BMP signaling in a sample from a subject harboring a mutation in the BMP signaling pathway, e.g., an ENG, ALK1 or Smad4 mutation. In an embodiment, the agent is a compound of Formula (I), (II), compound (A), compound (B), or compound (C) or a pharmaceutically acceptable salt thereof.

The phrase "enhance BMP signaling" or "potentiate BMP signaling" as used herein refers to the ability of an agent, e.g. a compound of Formula (I), (II), compound (A), compound (B), or compound (C) or a pharmaceutically acceptable salt thereof, to sequester FKBP12 and potentiate BMP signaling through sensitization or de-repression. In an embodiment, BMP signaling is enhanced to a level that is at least about 10%, at least about 15%, at least about 20%, about 25%, about 30%, about 35% about 40%, about 45%, about 50%, about 55%, about 60%, about 65%, about 70%, about 75%, about 80%, about 85%, about 90%, about 95%, about 100%, about 120%, about 150%, about 200%, about 250%, about 300%, about 350%, about 400%, about 450%, or about 500% more than the BMP signaling in a sample from a subject harboring a mutation in the BMP signaling pathway, e.g., an ENG, ALK1 or Smad4 mutation.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment, "treat", "treating" or "treatment" refers to alleviating or ameliorating at least one physical parameter including those which may not be discernible by the patient. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of a compound of Formula (I), (II), compound (A), compound (B), or compound (C) or a pharmaceutically acceptable salt thereof can be present in racemic or enantiomerically enriched, for example the (R)-, (S)- or (RS)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of Formula (I), (II), compound (A), compound (B), or compound (C) or a pharmaceutically acceptable salt thereof can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, a compound of Formula (I), (II), compound (A), compound (B), or compound (C), including their salts, can also be obtained in the form of their hydrates, or include other solvents used for their crystallization. The compound of Formula (I), (II), compound (A), compound (B), or compound (C) or a pharmaceutically acceptable salt thereof may inherently or by design form solvates with pharmaceutically acceptable solvents (including water); therefore, it is intended that the invention embrace both solvated and unsolvated forms. The term "solvate" refers to a molecular complex of a compound of Formula (I), (II), compound (A), compound (B), or compound (C) or a pharmaceutically acceptable salt thereof (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compound of Formula (I), (II), compound (A), compound (B), or compound (C), including salts, hydrates and solvates thereof, may inherently or by design form polymorphs.

In another aspect, the disclosure provides a pharmaceutical composition comprising a compound of Formula (I), (II), compound (A), compound (B), or compound (C) or a pharmaceutically acceptable salt thereof, and a pharmaceutically acceptable carrier. In a further embodiment, the pharmaceutical composition comprises at least two pharmaceutically acceptable carriers, such as those described herein. For purposes of the disclosure, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the disclosure can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

Tablets may be either film coated or enteric coated according to methods known in the art.

Suitable compositions for oral administration include an effective amount of a compound of Formula (I), (II), compound (A), compound (B), or compound (C) or a pharmaceutically acceptable salt thereof in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin through the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant. Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of Formula (I), (II), compound (A), compound (B), or compound (C) or a pharmaceutically acceptable salt thereof, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of Formula (I), (II), compound (A), compound (B), or compound (C) or a pharmaceutically acceptable salt thereof to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The compound of Formula (I), (II), compound (A), compound (B), or compound (C) in free form or in pharmaceutically acceptable salt form, exhibit valuable pharmacological properties, e.g. BMP potentiating properties, e.g. as indicated in vitro and in vivo tests as provided in the next sections, and are therefore indicated for therapy or for use as research chemicals, e.g. as tool compounds.

Methods of Use

A compound of Formula (I), (II), compound (A), compound (B), or compound (C) or a pharmaceutically acceptable salt thereof may be useful in the treatment of the diseases and disorders described herein. In an embodiment, the disease or disorder is associated with deficient BMP signalling and may be treated by potentiation of BMP. In an embodiment, the disorder is renal disease. In an embodiment, the renal disease is selected from the group consisting of diabetic nephropathy; AKI (acute kidney injury); and proteinuric diseases. In an embodiment, the disorder is selected from the group consisting of PAH (pulmonary arterial hypertension); HHT (hereditary hemorrhagic telangiectasia); iron overload anemia; fracture healing; macular degeneration (e.g., AMD (age-related macular degeneration)); glaucoma; dry eye; colitis; IBD (inflammatory bowel disease); juvenile polyposis syndrome; wound healing; fibrosis (e.g., lung, liver and kidney); skeletal muscle neurogenic atrophy; Alagille syndrome; and biliary atresia.

In an embodiment, the disclosure provides a method of treatment comprising a compound of Formula (I), (II), compound (A), compound (B), or compound (C) or a pharmaceutically acceptable salt thereof. In an embodiment, the therapy is selected from a disease which may be treated by potentiation of BMP signaling. In an embodiment, the disorder is renal disease. In an embodiment, the renal disease is selected from the group consisting of diabetic nephropathy; AKI (acute kidney injury); and proteinuric diseases. In an embodiment, the disorder is selected from the group consisting of PAH (pulmonary arterial hypertension); HHT (hereditary hemorrhagic telangiectasia); iron overload anemia; fracture healing; macular degeneration (e.g., AMD (age-related macular degeneration)); glaucoma; dry eye; colitis; IBD (inflammatory bowel disease); juvenile polyposis syndrome; wound healing; fibrosis (e.g., lung, liver and kidney); skeletal muscle neurogenic atrophy; Alagille syndrome; and biliary atresia.

In an embodiment, the disease is HHT (hereditary hemorrhagic telangiectasia).

In an embodiment, the disease is pulmonary arterial hypertension (PAH).

In an embodiment, the disease is proteinuric kidney disease or acute kidney injury (AKI).

In an embodiment, the disease is iron overload anemia.

In an embodiment, the disease is fracture healing.

In an embodiment, the disease is glaucoma.

In an embodiment, the disease is dry eye.

In an embodiment, the disease is juvenile polyposis syndrome.

In an embodiment, the disease is skeletal muscle neurogenic atrophy.

In an embodiment, the disease is lung, liver or kidney fibrosis.

In an embodiment, the disease is Alagille syndrome.

In an embodiment, the disease is Biliary Atresia.

Further, the disclosure provides the use of a compound of Formula (I), (II), compound (A), compound (B), or compound (C) or a pharmaceutically acceptable salt thereof in therapy. In a further embodiment, the therapy is selected from a disease which may be treated by potentiation of BMP signaling. In another embodiment, the disease is selected from the afore-mentioned list, suitably Hemorrhagic Telangiectasia (HHT).

Further, the disclosure provides the use of a compound of Formula (I), (II), compound (A), compound (B), or compound (C) or a pharmaceutically acceptable salt thereof in therapy. In a further embodiment, the therapy is selected from a disease which may be treated by potentiation of BMP signaling. In another embodiment, the disease is selected from the afore-mentioned list, suitably pulmonary arterial hypertension (PAH).

Further, the disclosure provides the use of a compound of Formula (I), (II), compound (A), compound (B), or compound (C) or a pharmaceutically acceptable salt thereof in therapy. In a further embodiment, the therapy is selected from a disease which may be treated by potentiation of BMP signaling. In another embodiment, the disease is selected from the afore-mentioned list, suitably proteinuric kidney disease and acute kidney injury.

Further, the disclosure provides the use of a compound of Formula (I), (II), compound (A), compound (B), or compound (C) or a pharmaceutically acceptable salt thereof in therapy. In a further embodiment, the therapy is selected from a disease which may be treated by potentiation of BMP signaling. In another embodiment, the disease is selected from the afore-mentioned list, suitably iron overload anemia.

Further, the disclosure provides the use of a compound of Formula (I), (II), compound (A), compound (B), or compound (C) or a pharmaceutically acceptable salt thereof in therapy. In a further embodiment, the therapy is selected from a disease which may be treated by potentiation of BMP signaling. In another embodiment, the disease is selected from the afore-mentioned list, suitably fracture healing.

Further, the disclosure provides the use of a compound of Formula (I), (II), compound (A), compound (B), or compound (C) or a pharmaceutically acceptable salt thereof in therapy. In a further embodiment, the therapy is selected from a disease which may be treated by potentiation of BMP signaling. In another embodiment, the disease is selected from the afore-mentioned list, suitably glaucoma.

Further, the disclosure provides the use of a compound of Formula (I), (II), compound (A), compound (B), or compound (C) or a pharmaceutically acceptable salt thereof in therapy. In a further embodiment, the therapy is selected from a disease which may be treated by potentiation of BMP signaling. In another embodiment, the disease is selected from the afore-mentioned list, suitably dry eye.

Further, the disclosure provides the use of a compound of Formula (I), (II), compound (A), compound (B), or compound (C) or a pharmaceutically acceptable salt thereof in therapy. In a further embodiment, the therapy is selected from a disease which may be treated by potentiation of BMP signaling. In another embodiment, the disease is selected from the afore-mentioned list, suitably juvenile polyposis syndrome.

Further, the disclosure provides the use of a compound of Formula (I), (II), compound (A), compound (B), or compound (C) or a pharmaceutically acceptable salt thereof in therapy. In a further embodiment, the therapy is selected from a disease which may be treated by potentiation of BMP. In another embodiment, the disease is selected from the afore-mentioned list, suitably skeletal muscle neurogenic atrophy.

Further, the disclosure provides the use of a compound of Formula (I), (II), compound (A), compound (B), or compound (C) or a pharmaceutically acceptable salt thereof in therapy. In a further embodiment, the therapy is selected from a disease which may be treated by potentiation of BMP signaling. In another embodiment, the disease is selected from the afore-mentioned list, suitably lung, liver and kidney fibrosis.

Further, the disclosure provides the use of a compound of Formula (I), (II), compound (A), compound (B), or compound (C) or a pharmaceutically acceptable salt thereof in therapy. In a further embodiment, the therapy is selected from a disease which may be treated by potentiation of BMP. In another embodiment, the disease is selected from the afore-mentioned list, suitably Alagille syndrome.

Further, the disclosure provides the use of a compound of Formula (I), (II), compound (A), compound (B), or compound (C) or a pharmaceutically acceptable salt thereof in therapy. In a further embodiment, the therapy is selected from a disease which may be treated by potentiation of BMP. In another embodiment, the disease is selected from the afore-mentioned list, suitably Biliary Atresia.

Further, the disclosure provides the use of a compound of Formula (I), (II), compound (A), compound (B), or compound (C) or a pharmaceutically acceptable salt thereof for the manufacture of a medicament. In a further embodiment, the medicament is for treatment of a disease which may be treated by potentiation of BMP signaling. In another embodiment, the disease is selected from the afore-mentioned list, suitably Hemorrhagic Telangiectasia (HHT).

The pharmaceutical composition or combination of the disclosure can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the disclosure can be assessed by the following methods.

The compound of Formula (I), (II), compound (A), compound (B), or compound (C) or a pharmaceutically acceptable salt thereof may be administered either simultaneously with, or before or after, one or more other therapeutic agent. The compound of Formula (I), (II), compound (A), compound (B), or compound (C) or a pharmaceutically acceptable salt thereof may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the disclosure provides a product comprising a compound of Formula (I), (II), compound (A), compound (B), or compound (C) or a pharmaceutically acceptable salt thereof and at least one other therapeutic agent as a combined preparation for simultaneous, separate or sequential use in therapy. In one embodiment, the therapy is the treatment of a disease or condition mediated by BMP signaling. Products provided as a combined preparation include a composition comprising the compound of Formula (I), (II), compound (A), compound (B), or compound (C) or a pharmaceutically acceptable salt thereof and the other therapeutic agent(s) together in the same pharmaceutical composition, or the compound of Formula (I), (II), compound (A), compound (B), or compound (C) or a pharmaceutically acceptable salt thereof and the other therapeutic agent(s) in separate form, e.g. in the form of a kit.

In one embodiment, the disclosure provides a pharmaceutical composition comprising a compound of Formula (I), (II), compound (A), compound (B), or compound (C) or a pharmaceutically acceptable salt thereof and another therapeutic agent(s). Optionally, the pharmaceutical composition may comprise a pharmaceutically acceptable carrier, as described above.

In one embodiment, the disclosure provides a kit comprising two or more separate pharmaceutical compositions, at least one of which contains a compound of Formula (I), (II), compound (A), compound (B), or compound (C) or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the disclosure may be used for administering different dosage forms, for example, oral and parenteral, for administering the separate compositions at different dosage intervals, or for titrating the separate compositions against one another. To assist compliance, the kit of the disclosure typically comprises directions for administration.

In the combination therapies of the disclosure, the compound of Formula (I), (II), compound (A), compound (B), or compound (C) or a pharmaceutically acceptable salt thereof and the other therapeutic agent may be manufactured and/or formulated by the same or different manufacturers. Moreover, the compound of Formula (I), (II), compound (A), compound (B), or compound (C) or a pharmaceutically acceptable salt thereof and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of Formula (I), (II), compound (A), compound (B), or compound (C) or a pharmaceutically acceptable salt thereof for treating a disease or condition mediated by BMP, wherein the medicament is prepared for administration with another therapeutic agent. The disclosure also provides the use of another therapeutic agent for treating a disease or condition mediated by BMP, wherein the medicament is administered with a compound of Formula (I), (II), compound (A), compound (B), or compound (C) or a pharmaceutically acceptable salt thereof.

The disclosure also provides a compound of Formula (I), (II), compound (A), compound (B), or compound (C) or a pharmaceutically acceptable salt thereof for use in a method of treating a disease or condition mediated by BMP, wherein the compound of Formula (I), (II), compound (A), compound (B), or compound (C) or a pharmaceutically acceptable salt thereof is prepared for administration with another therapeutic agent. The disclosure also provides another therapeutic agent for use in a method of treating a disease or condition mediated by BMP, wherein the other therapeutic agent is prepared for administration with a compound of Formula (I), (II), compound (A), compound (B), or compound (C) or a pharmaceutically acceptable salt thereof. The disclosure also provides a compound of Formula (I), (II), compound (A), compound (B), or compound (C) or a pharmaceutically acceptable salt thereof for use in a method of treating a disease or condition mediated by BMP, wherein the compound of Formula (I), (II), compound (A), compound (B), or compound (C) or a pharmaceutically acceptable salt thereof is administered with another therapeutic agent. The disclosure also provides another therapeutic agent for use in a method of treating a disease or condition mediated by BMP, wherein the other therapeutic agent is administered with a compound of Formula (I), (II), compound (A), compound (B), or compound (C) or a pharmaceutically acceptable salt thereof.

The disclosure also provides the use of a compound of Formula (I), (II), compound (A), compound (B), or compound (C) or a pharmaceutically acceptable salt thereof for treating a disease or condition mediated by BMP, wherein the patient has previously (e.g. within 24 hours) been treated with another therapeutic agent. The disclosure also provides the use of another therapeutic agent for treating a disease or condition mediated by BMP, wherein the patient has previously (e.g. within 24 hours) been treated with a compound of Formula (I), (II), compound (A), compound (B), or compound (C) or a pharmaceutically acceptable salt thereof.

In one embodiment, the other therapeutic agent is selected from: an anti-VEGF antibody, e.g. Bevacizumab, a soy protein isolate, an antifibrionic, e.g. tranexamic acid, a CRBN modulator, e.g. thalidomide, bFGF induced antiangiogenic, VEGF induced antiangiogenic, a somastatin mimic, e.g. ocreotide, a GHIH mimic, an estrogen receptor antagonist, e.g. tamoxifen and pomalidomide.

In one embodiment, there is provided a product comprising a compound of Formula (I), (II), compound (A), compound (B), or compound (C) or a pharmaceutically acceptable salt thereof and an anti-VEGF antibody as a combined preparation for simultaneous, separate or sequential use in therapy.

In one embodiment, there is provided a product comprising a compound of Formula (I), (II), compound (A), compound (B), or compound (C) or a pharmaceutically acceptable salt thereof and a soy protein isolate as a combined preparation for simultaneous, separate or sequential use in therapy.

In one embodiment, there is provided a product comprising a compound of Formula (I), (II), compound (A), compound (B), or compound (C) or a pharmaceutically acceptable salt thereof and an antifibrionic as a combined preparation for simultaneous, separate or sequential use in therapy.

In one embodiment, there is provided a product comprising a compound of Formula (I), (II), compound (A), compound (B), or compound (C) or a pharmaceutically acceptable salt thereof and a CRBN modulator as a combined preparation for simultaneous, separate or sequential use in therapy.

In one embodiment, there is provided a product comprising a compound of Formula (I), (II), compound (A), compound (B), or compound (C) or a pharmaceutically acceptable salt thereof and a bFGF induced antiangiogenic as a combined preparation for simultaneous, separate or sequential use in therapy.

In one embodiment, there is provided a product comprising a compound of Formula (I), (II), compound (A), compound (B), or compound (C) or a pharmaceutically acceptable salt thereof and a VEGF induced antiangiogenic as a combined preparation for simultaneous, separate or sequential use in therapy.

In one embodiment, there is provided a product comprising a compound of Formula (I), (II), compound (A), compound (B), or compound (C) or a pharmaceutically acceptable salt thereof and a somastatin mimic as a combined preparation for simultaneous, separate or sequential use in therapy.

In one embodiment, there is provided a product comprising a compound of Formula (I), (II), compound (A), compound (B), or compound (C) or a pharmaceutically acceptable salt thereof and a GHIH mimic as a combined preparation for simultaneous, separate or sequential use in therapy.

In one embodiment, there is provided a product comprising a compound of Formula (I), (II), compound (A), compound (B), or compound (C) or a pharmaceutically acceptable salt thereof and an estrogen receptor antagonist as a combined preparation for simultaneous, separate or sequential use in therapy.

EXAMPLES

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

Analytical Conditions

HRMS column: Experimental: LC-UV/ESI-MS data was recorded on an Acquity G2 Xevo QTof-Rs(FWHM)>20000 Eluent A: Water+0.1% Formic Acid Eluent B: Acetonitrile+0.1% Formic Acid Macrocycle column: Waters BEH C18 2.1×50 mm 1.7 um 60 C: Conditions: 20-90% Acetonitrile:Methanol:Water (80:15:5) in 10 mM Ammonium formate with 0.1% Formic Acid 1 mL/min List of Abbreviations
HGII=Hoveyda Grubbs $2^{nd}$ Generation catalyst
DCE=1,2-Dichloroethane
MeOH=methanol
r.t.=room temperature

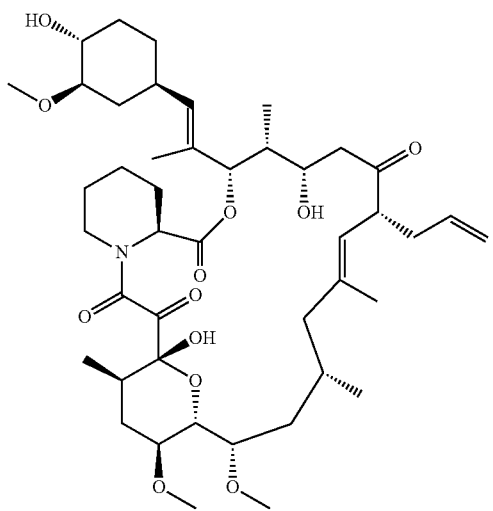

FK-506 (Tacrolimus)

(also known as FK-506 or fujimycin, trade names Prograf®, Advagraf®, Protopic®) is an immunosuppressive drug used mainly after allogeneic organ transplant to lower the risk of organ rejection. It achieves this by inhibiting the production of interleukin-2, a molecule that promotes the development and proliferation of T cells, which are vital to the body's learned (or adaptive) immune response. Chemically it is a 23-membered macrolide lactone that was first discovered in 1987 from the fermentation broth of a Japanese soil sample that contained the bacterium *Streptonyces tsukubaensis*.

Example 1. Synthesis of Compound A

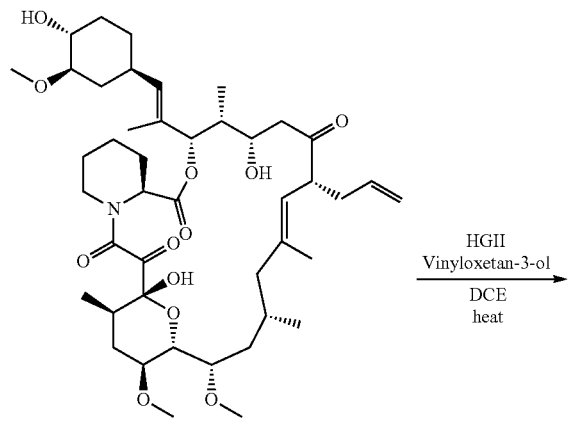

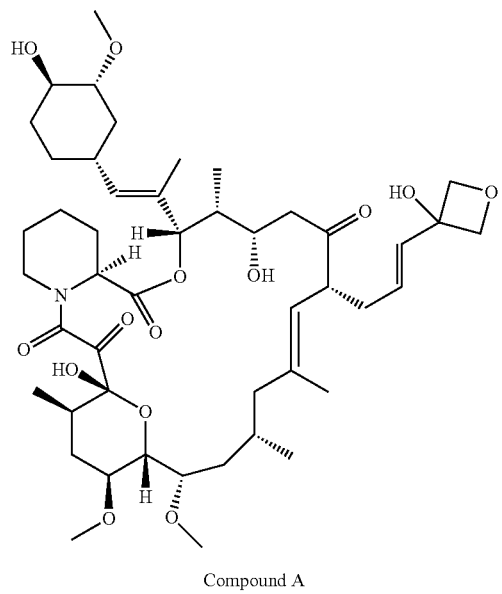

Compound A

To a solution of FK506 (50 mg, 0.062 mmol) in DCE (Volume: 622 μl) in a 5 mL microwave vial was added HGII (3.90 mg, 6.22 μmol) and vinyloxetan-3-ol (125 mg, 1.244 mmol). The solution was stirred for 30 seconds and then irradiated at 150° C. for 5 minutes in a microwave, over which time the reaction turned amber in color.

The reaction mixture was filtered and rinsed with MeOH. The crude reaction was concentrated under reduced pressure and resuspended in a minimal amount of MeOH.

The reaction was purified by SFC (SFC Instrument: Thar 80, Column: Princeton 2-EP 20×150 mm 5 μm, Flow Rate: 80 g/min, Cosolvent: 12% Methanol, Detection: 205 nm, BPR set point: 125 bar (Oven 40° C.)) to afford the target compound as a cream colored solid (21 mg, 39% yield). $^1$H NMR (400 MHz, CDCl$_3$), Diagnostic analysis shows the disappearance of terminal olefinic peaks between 6 and 7 ppm. $^{13}$C NMR shows the addition of peaks between 40-80 ppm, corresponding to an aliphatic carbon addition. $^{13}$C NMR (major isomer in MeOD) δ: 10.78, 13.36, 15.96, 16.52, 20.21, 22.14, 25.37, 27.25, 28.16, 28.91, 31.83, 33.55, 35.17, 35.90, 36.17, 36.79, 40.25, 41.67, 45.54, 46.50, 47.71, 53.79, 54.47, 56.18, 56.68, 57.39, 55.70, 57.90, 70.32, 73.86, 74.63, 75.12, 76.93, 81.38, 85.21, 85.25, 99.06, 124.20, 128.51, 133.05, 133.86, 134.32, 140.23, 167.51, 170.65, 198.47, 212.39. HRMS Calcd. for $C_{47}H_{74}NO_{14}$ (M+H) 876.5109, found 876.5105.

Example 2. Synthesis of Compound B

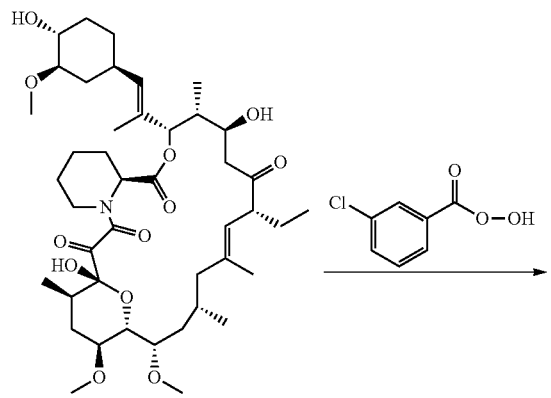

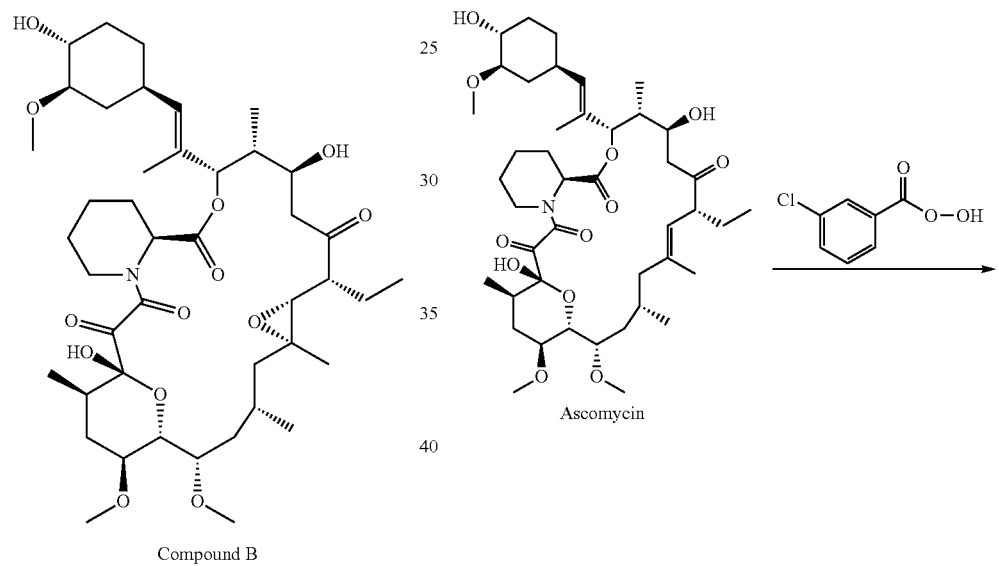

Compound B

To a 0.03 M solution of Ascomycin (1 eq.) in anhydrous DCM, at 0° C., was added mCPBA (77% moist powder, 1.2 eq.). The reaction mixture was stirred at 0° C. for 1.5 h, then at r.t. overnight. The reaction mixture was quenched with sat. $Na_2SO_3$ aqueous solution and diluted with EtOAc. The organic layer was washed with sat. $NaHCO_3$ aqueous solution and brine. Then the organic layer was concentrated, and the residue was purified by silica gel chromatography, eluting with Heptane/EtOAc (40/60 to 20/80). The collected fractions were purified a second time by reverse phase silica gel chromatography (0.1% $NH_4OH$ in Water/Acetonitrile, gradient 30-80% of Acetonitrile).

The collected fractions were lyophilized. The dried solid was purified with SFC to provide compound B with >98% purity and 7-8% yield. (SFC Instrument: Thar 80, Column: Kinetex Biphenyl 30×150 mm 5 um, Flow Rate: 80 g/min, Cosolvent: 12% Methanol, Detection: 205 nm, BPR set point: 125 bar (Oven 40° C.)). $^{13}C$ NMR (major isomer in $d_6$-DMSO) δ: 10.32, 11.29, 11.54, 15.60, 15.65, 18.31, 19.76, 23.57, 23.73, 24.76, 27.75, 30.31, 31.55, 32.37, 33.79, 34.73, 35.81, 35.97, 37.99, 39.69, 46.51, 50.54, 52.63, 54.87, 55.61, 56.46, 57.05, 60.02, 62.58, 66.58, 71.24, 72.32, 72.56, 74.37, 82.94, 83.07, 97.88, 129.88, 135.17, 165.64, 168.62, 197.48, 212.43. HRMS Calcd. for $C_{43}H_{69}NO_{13}$ 807.4769, found 807.4769.

Example 3. Synthesis of Compound C

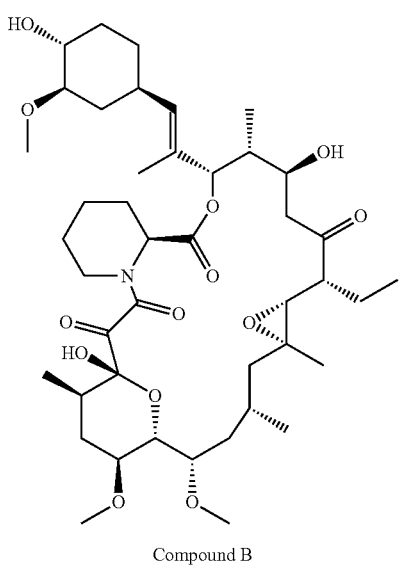

Compound B

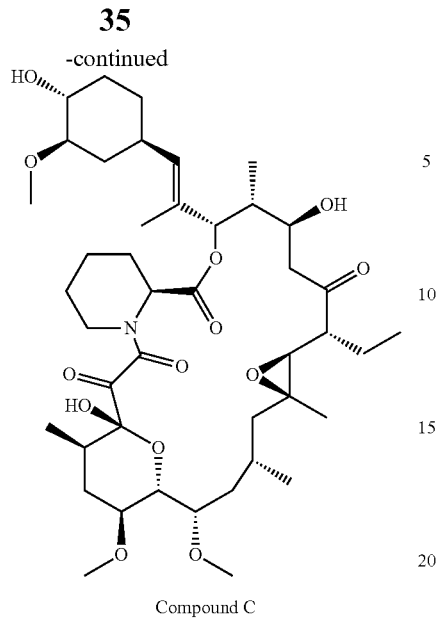

Compound C

To 0.03 M solution of Ascomycin (1 eq.) in anhydrous DCM, at 0° C., was added mCPBA (77% moist powder, 1.2 eq.). The reaction mixture was stirred at 0° C. for 1.5 h, then at r.t. overnight. The reaction mixture was quenched with saturated $Na_2SO_3$ aqueous solution and diluted with EtOAc. The organic layer was washed with saturated $NaHCO_3$ aqueous solution and brine. Then the organic layer was concentrated, the residue was purified by silica gel chromatography, eluting with Heptane/EtOAc (40/60 to 20/80). The first collected fractions were purified with HPLC (40-70% ACN:MeOH:Water (80:15:5) in 10 mM Ammonium formate with 0.04% Formic acid). The fractions were lyophilized to provide compound C. HRMS Calcd. for $C_{43}H_{69}NO_{13}$ 807.48, found 807.48. HRMS retention time: 2.96 min. Compound B HRMS retention time: 2.75 min.

The activity of a compound according to the present invention can be assessed by the following methods.

Example 4. BMP Activity

Reporter Cell Lines

C2C12-IDBRE-luciferase reporter line was established by infecting C2C12 cells with lentiviruses with IDBRE-luciferase pLenti6 plasmid with Blasticidin resistance.

Reporter Assays

C2C12-IDBRE-luciferase cells were plated to 384-well plate at 5000 cells in 36 μl DMEM plus 10% FBS at day 0. Cells were treated with different doses of compounds at day 1. Bright-Glo™ Luciferase Assay (Promega, catalog # E2650) was performed with EnVision plate reader (PerkinElmer) 24 hours after treatment at day 2. 0% activity is equal to DMSO control. 100% activity means Luminescence reading for a compound is 200% of luminescence reading of DMSO control. The formula to calculate the activity is:

100*(Luminescence_compound−Luminescence_DMSO)/Luminescence_DMSO

| Structure Name | Chemical Structure | Qualified absolute AC50 (μM) |
|---|---|---|
| FK-506 | 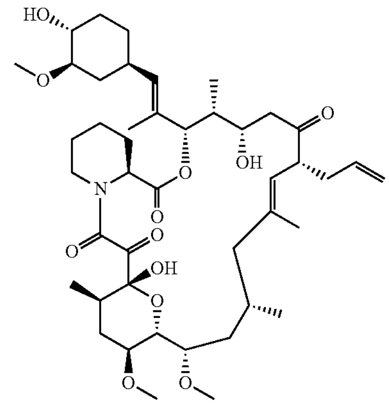 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC] | 0.024 |
| Compound C | 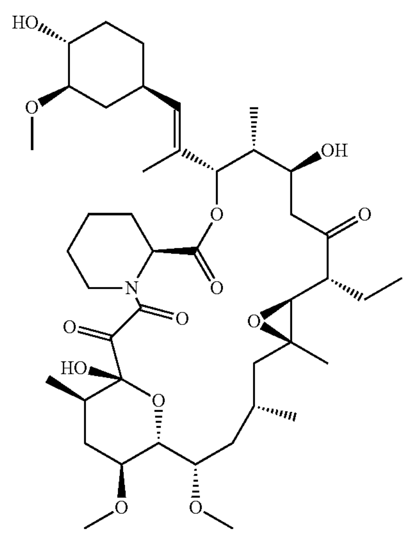 [SMILES: CC[C@H]1C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C[C@@H](C)C[C@]3(C)O[C@@H]13)[C@@H](OC)C[C@H]2C] | 0.201 |
| Compound B | 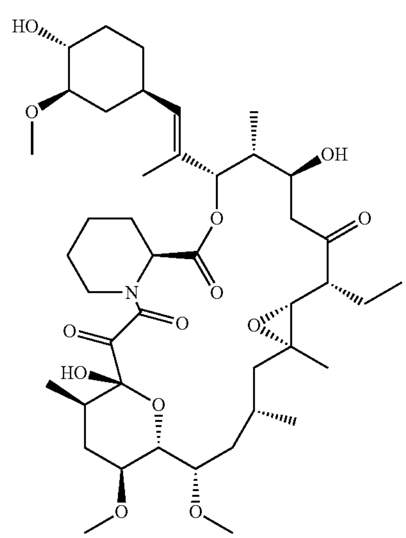 [SMILES: CC[C@H]1C(=O)C[C@H](O)[C@@H](C)[C@@H](/C(C)=C/[C@@H]2CC[C@@H](O)[C@H](OC)C2)OC(=O)[C@@H]2CCCCN2C(=O)C(=O)[C@]2(O)O[C@H]([C@@H](OC)C[C@@H](C)C[C@@]3(C)O[C@H]13)[C@@H](OC)C[C@H]2C] | 0.024 |

37
-continued

| Structure Name | Chemical Structure | Qualified absolute AC50 (μM) |
|---|---|---|
| Compound A | (structure shown) | 0.091 |

Example 5. Calcineurin Inhibition

Reporter Cell Lines

NFAT-luciferase reporter line was established by transfecting NFAT-luciferase/pTranslucent (Panomics #LR0050) and Puromycin-resistance plasmid together into 293T cells.

Reporter Assays

293T-NFAT-luciferase cells were plated to 384-well plate at 10000 cells in 32 μl DMEM plus 10% FBS at day 0. Cells were treated with different doses of compounds at day 1. Half an hour after compound treatment, 293T-NFAT-luciferase cells were co-treated with 100 ng/ml PMA (PHORBOL 12-MYRISTATE 13-ACETAT, Sigma, catalog #P8139-1MG) and 1 μM Ionomycin (Sigma, catalog #10634-1MG). Bright-Glo™ Luciferase Assay (Promega, catalog # E2650) was performed with EnVision plate reader (PerkinElmer) 24 hours after treatment at day 2.

| Structure Name | NFAT-luc IC50 (nM) |
|---|---|
| FK-506 | 0.05 |
| Compound C | 33 |
| Compound B | >50,000 |
| Compound A | >50,000 |

Having thus described several aspects of several embodiments, it is to be appreciated various alterations, modifica-

38 tions, and improvements will readily occur to those skilled in the art. Such alterations, modifications, and improvements are intended to be part of this disclosure, and are intended to be within the spirit and scope of the invention. Accordingly, the foregoing description and drawings are by way of example only.

We claim:

1. A compound of Formula (I) or a pharmaceutically acceptable salt thereof, wherein:

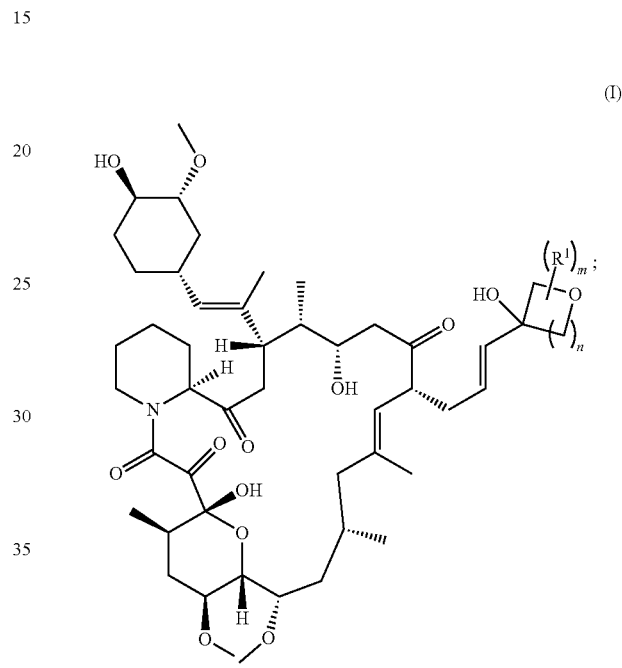

(I)

each $R^1$ is independently selected from the group consisting of halo, cyano, $C_{1-6}$ alkyl, $C_{1-6}$ alkoxyl, $C_{2-6}$ alkenyl, $C_{2-6}$ alkynyl, heteroC$_{1-10}$ alkyl, and $C_{1-6}$ haloalkyl;

n is 1, 2, 3, 4, or 5; and m is 0, 1, 2, 3, or 4.

2. The compound of claim 1 or a pharmaceutically acceptable salt thereof, wherein n is 1, 2 or 3.

3. The compound of claim 1 or a pharmaceutically acceptable salt thereof, wherein n is 1.

4. The compound of claim 1 or a pharmaceutically acceptable salt thereof, wherein $R^1$ is selected from the group consisting of halo and $C_{1-6}$ alkyl.

5. The compound of claim 1 or a pharmaceutically acceptable salt thereof, wherein m is 0 or 1.

6. The compound of claim 1 or a pharmaceutically acceptable salt thereof, wherein m is 0.

7. A compound of Formula (A) or a pharmaceutically acceptable salt thereof:

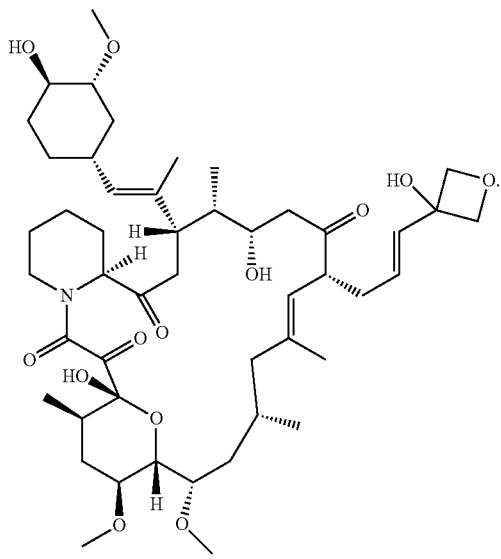

(A)

8. A compound of Formula (II) or a pharmaceutically acceptable salt thereof:

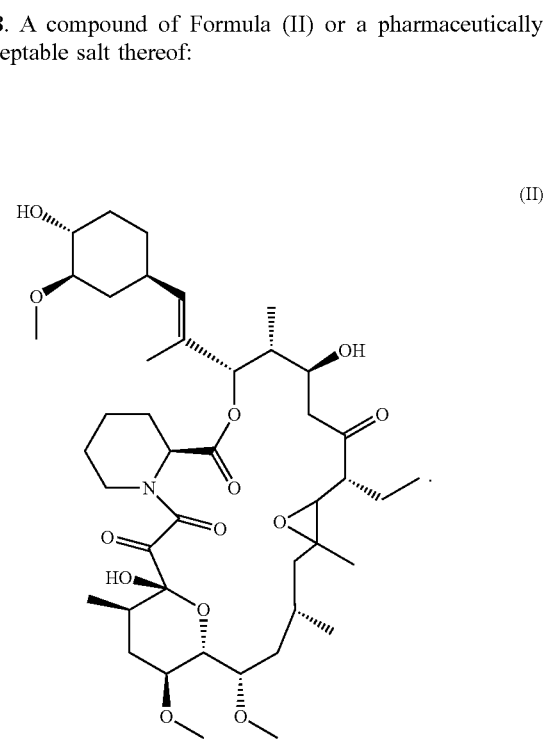

(II)

9. The compound of claim 8 or a pharmaceutically acceptable salt thereof having Formula (B):

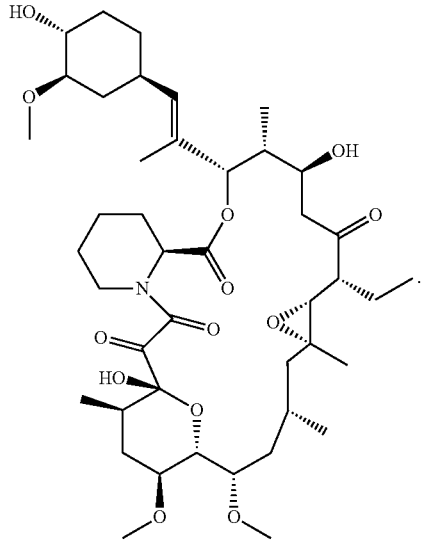

(B)

10. The compound of claim 8 or a pharmaceutically acceptable salt thereof having Formula (C):

(C)

11. A pharmaceutical composition comprising a therapeutically effective amount of a compound of claim 7 or a pharmaceutically acceptable salt thereof, and one or more pharmaceutically acceptable carriers.

12. A pharmaceutical composition comprising a therapeutically effective amount of a compound of claim 8 or a pharmaceutically acceptable salt thereof, and one or more pharmaceutically acceptable carriers.

13. A pharmaceutical composition comprising a therapeutically effective amount of a compound of claim 9 or a pharmaceutically acceptable salt thereof, and one or more pharmaceutically acceptable carriers.

14. A pharmaceutical composition comprising a therapeutically effective amount of a compound of claim 10 or a pharmaceutically acceptable salt thereof, and one or more pharmaceutically acceptable carriers.

* * * * *